(12) United States Patent
Hadjicostis (10) Patent No.: US 10,188,368 B2
(45) Date of Patent: Jan. 29, 2019

(54) IMAGE GUIDED INTRAVASCULAR THERAPY CATHETER UTILIZING A THIN CHIP MULTIPLEXOR

(71) Applicant: Andreas Hadjicostis, Fairview, TX (US)

(72) Inventor: Andreas Hadjicostis, Fairview, TX (US)

(*) Notice: Subject to any disclaimer, the term of this patent is extended or adjusted under 35 U.S.C. 154(b) by 0 days.

(21) Appl. No.: 15/633,716

(22) Filed: Jun. 26, 2017

(65) Prior Publication Data

US 2018/0368805 A1    Dec. 27, 2018

(51) Int. Cl.
*A61B 8/00* (2006.01)
*A61B 8/12* (2006.01)
*A61B 18/14* (2006.01)
*A61B 18/00* (2006.01)
*A61B 90/00* (2016.01)

(52) U.S. Cl.
CPC .......... *A61B 8/12* (2013.01); *A61B 8/445* (2013.01); *A61B 8/4483* (2013.01); *A61B 18/1492* (2013.01); *A61B 2018/00386* (2013.01); *A61B 2018/00577* (2013.01); *A61B 2018/00982* (2013.01); *A61B 2090/065* (2016.02)

(58) Field of Classification Search
CPC ......... A61B 8/12; A61B 8/445; A61B 8/4483; A61B 18/1492; A61B 2090/065; A61B 2018/00386; A61B 2018/00577; A61B 2018/00982
See application file for complete search history.

(56) References Cited

U.S. PATENT DOCUMENTS

| | | |
|---|---|---|
| 3,827,115 A | 8/1974 | Bom |
| 3,938,502 A | 2/1976 | Bom |
| 4,446,395 A | 5/1984 | Hadjicostis |
| 4,532,924 A | 8/1985 | Auth et al. |
| 4,643,186 A | 2/1987 | Rosen et al. |
| 4,682,596 A | 7/1987 | Bales et al. |
| 4,794,931 A | 1/1989 | Yock |
| 4,939,826 A | 7/1990 | Schoup |
| 5,010,886 A | 4/1991 | Passafaro et al. |
| 5,098,431 A | 3/1992 | Rydell |

(Continued)

FOREIGN PATENT DOCUMENTS

| | | |
|---|---|---|
| CN | 106037803 A | 10/2016 |
| EP | 1717601 | 2/2008 |

(Continued)

*Primary Examiner* — Joseph M Santos Rodriguez
(74) *Attorney, Agent, or Firm* — Timothy E. Siegel Patent Law, PLLC; Timothy E. Siegel (57) ABSTRACT

A medical device that includes an array of ultrasound elements and an integrated circuit, proximal to the ultrasound elements, having a thickness of less than 40 μm, and having an array of ultrasound element driving-and-receiving contacts, matching the array of ultrasound elements and collectively electrically connected to each of the ultrasound elements. The integrated circuit also having a set of input-output signal contacts, the set being collectively switchable into contact with any one of a set of predefined blocks of driving-and-receiving contacts, and a set of control contacts, wherein inputs received by the control contacts collectively command some aspect of chip operation. The medical device further includes a set a protective covering.

18 Claims, 8 Drawing Sheets

(56) References Cited

U.S. PATENT DOCUMENTS

| | | |
|---|---|---|
| 5,159,931 A | 11/1992 | Pini |
| 5,176,141 A | 1/1993 | Bom et al. |
| 5,240,003 A | 8/1993 | Lancee et al. |
| 5,291,893 A | 3/1994 | Slayton |
| 5,327,905 A | 7/1994 | Avitall |
| 5,359,760 A | 11/1994 | Busse et al. |
| 5,425,364 A * | 6/1995 | Imran ................ A61B 5/0422 |
| | | 600/374 |
| 5,454,809 A | 10/1995 | Janssen |
| 5,592,730 A | 1/1997 | Greenstein et al. |
| 5,622,177 A | 4/1997 | Breimesser et al. |
| 5,626,576 A | 5/1997 | Janssen |
| 5,749,914 A | 5/1998 | Janssen |
| 5,771,895 A | 6/1998 | Slager |
| 5,788,636 A | 8/1998 | Curley |
| 5,840,030 A | 11/1998 | Ferek-Petric et al. |
| 5,840,031 A | 11/1998 | Crowley |
| 5,857,974 A | 1/1999 | Eberle et al. |
| 5,893,832 A | 4/1999 | Song |
| 5,924,993 A | 7/1999 | Hadjicostis et al. |
| 5,935,108 A | 8/1999 | Kathoh et al. |
| 6,047,216 A | 4/2000 | Carl et al. |
| 6,066,096 A | 5/2000 | Smith et al. |
| 6,099,524 A | 8/2000 | Lipson et al. |
| 6,356,790 B1 | 3/2002 | Maguire et al. |
| 6,394,956 B1 | 5/2002 | Chandrasekaran et al. |
| 6,560,472 B2 | 5/2003 | Hill et al. |
| 6,572,551 B1 | 6/2003 | Smith et al. |
| 6,582,369 B1 | 6/2003 | Huang et al. |
| 6,582,423 B1 | 6/2003 | Thapliyal |
| 6,679,845 B2 | 1/2004 | Ritter et al. |
| 6,709,396 B2 | 3/2004 | Flesch et al. |
| 6,783,497 B2 | 8/2004 | Grenon et al. |
| 6,852,109 B2 | 2/2005 | Winston et al. |
| 6,858,006 B2 | 2/2005 | MacCarter et al. |
| 6,892,438 B1 | 5/2005 | Hill et al. |
| 6,899,682 B2 | 5/2005 | Eberle et al. |
| 6,925,693 B2 | 8/2005 | Takeuchi et al. |
| 6,962,567 B2 | 11/2005 | Eberle et al. |
| 6,972,018 B2 | 12/2005 | Ryan et al. |
| 6,994,674 B2 | 2/2006 | Sheljaskow et al. |
| 7,004,940 B2 | 2/2006 | Ryan et al. |
| 7,022,088 B2 | 4/2006 | Keast et al. |
| 7,045,108 B2 | 5/2006 | Jiang et al. |
| 7,053,530 B2 | 5/2006 | Baumgartner et al. |
| 7,060,033 B2 | 6/2006 | White et al. |
| 7,066,895 B2 | 6/2006 | Podany |
| 7,074,218 B2 | 7/2006 | Washington et al. |
| 7,112,196 B2 | 9/2006 | Brosch et al. |
| 7,115,092 B2 | 10/2006 | Park et al. |
| 7,156,812 B2 | 1/2007 | Seward et al. |
| 7,156,938 B2 | 1/2007 | Baumgartner et al. |
| 7,195,179 B2 | 3/2007 | Miller et al. |
| 7,226,417 B1 * | 6/2007 | Eberle ................ B06B 1/0633 |
| | | 29/25.35 |
| 7,519,410 B2 | 4/2009 | Taimisto et al. |
| 7,596,415 B2 | 9/2009 | Brabec et al. |
| 7,844,347 B2 | 11/2010 | Brabec et al. |
| 8,414,492 B2 | 4/2013 | Hadjicostis |
| 8,425,421 B2 | 4/2013 | Hadjicostis |
| 8,702,609 B2 | 4/2014 | Hadjicostis |
| 8,974,446 B2 | 3/2015 | Nguyen et al. |
| 9,138,290 B2 | 9/2015 | Hadjicostis |
| 2003/0055308 A1 | 3/2003 | Freimel et al. |
| 2004/0068191 A1 | 4/2004 | Seward |
| 2004/0092806 A1 | 5/2004 | Sagon et al. |
| 2004/0147920 A1 | 7/2004 | Keidar |
| 2004/0254471 A1 * | 12/2004 | Hadjicostis ............. A61B 8/12 |
| | | 600/459 |
| 2004/0254570 A1 | 12/2004 | Hadjicostis et al. |
| 2005/0033182 A1 | 2/2005 | Cerofolini |
| 2005/0107783 A1 | 5/2005 | Tom et al. |
| 2005/0159739 A1 | 7/2005 | Paul et al. |
| 2005/0228290 A1 | 10/2005 | Borovsky |
| 2005/0251127 A1 | 11/2005 | Brosch et al. |
| 2006/0030844 A1 | 2/2006 | Knight et al. |
| 2007/0167804 A1 | 7/2007 | Park et al. |
| 2007/0189761 A1 * | 8/2007 | Sudol ................ A61B 8/4483 |
| | | 396/316 |
| 2008/0200815 A1 * | 8/2008 | Van Der Steen ........ A61B 8/12 |
| | | 600/467 |
| 2013/0267853 A1 | 10/2013 | Dausch et al. |
| 2014/0180101 A1 | 6/2014 | Hadjicostis |
| 2015/0099976 A1 | 4/2015 | Ghaffari et al. |
| 2016/0008067 A1 | 1/2016 | Hadjicostis |
| 2016/0113633 A1 * | 4/2016 | Hadjicostis .......... A61B 8/4483 |
| | | 600/439 |
| 2016/0374710 A1 | 12/2016 | Sinelnikov et al. |

FOREIGN PATENT DOCUMENTS

| | | |
|---|---|---|
| EP | 2136603 | 12/2009 |
| JP | H02134149 A | 5/1990 |
| JP | H02140156 A | 5/1990 |
| KR | 20060112244 | 10/2006 |
| WO | 9519143 | 7/1995 |
| WO | 9745157 A1 | 12/1997 |
| WO | 9912489 | 3/1999 |

* cited by examiner

IMAGE GUIDED INTRAVASCULAR THERAPY CATHETER UTILIZING A THIN CHIP MULTIPLEXOR

BACKGROUND

U.S. Pat. No. 8,702,609, which is assigned to the assignee of the present application, discloses an image guided-therapy catheter that uses ultrasound to form an image of the interior of a blood vessel directly in front of the catheter, to determine the locations of plaque, and then permits the use of this information in driving a set of RF ablation electrodes to selectively ablate plaque, while avoiding damaging the interior surfaces of the blood vessel. A number of challenging issues are presented in the design of this type of device. Among these is the acoustic characteristics of the medical device and how to avoid harmful interference to the returning signal from signal that has reflected from the portion of the device proximal (that is, further back from the tip) to the ultrasound array.

Another troublesome issue in the design of the system is the multiplexing of the driving/receiving coax lines for the ultrasound elements. With a large array, it would be impossible to have a separate coax line for each element. Multiplexors, however, require an increasing number of control inputs for an increasing number of multiplexed lines. With catheter space at an extreme premium, fitting a high number of control lines into a catheter is also very problematic.

SUMMARY

The following embodiments and aspects thereof are described and illustrated in conjunction with systems, tools and methods which are meant to be exemplary and illustrative, not limiting in scope. In various embodiments, one or more of the above-described problems have been reduced or eliminated, while other embodiments are directed to other improvements.

In a first separate aspect, the present invention may take the form of a medical device that includes an array of ultrasound elements and an integrated circuit (IC) die, proximal to the ultrasound elements, having a thickness of less than 40 µm, and having an array of ultrasound element driving-and-receiving contacts, matching the array of ultrasound elements and collectively electrically connected to each of the ultrasound elements. The integrated circuit die also has a set of input-output signal contacts, the set being collectively switchable into contact with any one of a set of predefined blocks of driving-and-receiving contacts, and a set of control contacts, wherein inputs received by the control contacts collectively command some aspect of chip operation. The medical device further includes a tubular protective covering, which covers the ultrasound array and the IC die.

In a second separate aspect, the present invention may take the form of an intravenous ultrasound catheter, having an array of ultrasound elements near to a distal tip of the device. An integrated circuit, proximal to the ultrasound elements, having a thickness of less than 80 µm, and having an array of ultrasound element driving-and-receiving contacts, matching the array of ultrasound elements and collectively electrically connected to each of the ultrasound elements. The integrated circuit die also having a set of input-output signal contacts, the set being collectively switchable into contact with any one of a set of predefined blocks of driving-and-receiving contacts, and a set of control contacts, wherein inputs received by the control contacts collectively command some aspect of chip operation. A flex circuit assembly, proximal to the integrated circuit and including coax cables and a contact portion, made of contact portion material and having a set of contact pads connecting the input-output signal contacts to the coax cables. Backing material, directly proximal to the contact portion, thereby forms an interface and wherein the backing material and the contact portion material have substantial equal acoustic impedance, thereby preventing reflection at the interface. A tubular, flexible protective covering, covers the ultrasound array and the IC die.

In addition to the exemplary aspects and embodiments described above, further aspects and embodiments will become apparent by reference to the drawings and by study of the following detailed descriptions.

BRIEF DESCRIPTION OF THE DRAWINGS

Exemplary embodiments are illustrated in referenced drawings. It is intended that the embodiments and figures disclosed herein are to be considered illustrative rather than restrictive.

DETAILED DESCRIPTION OF THE PREFERRED EMBODIMENTS

Figure 1:
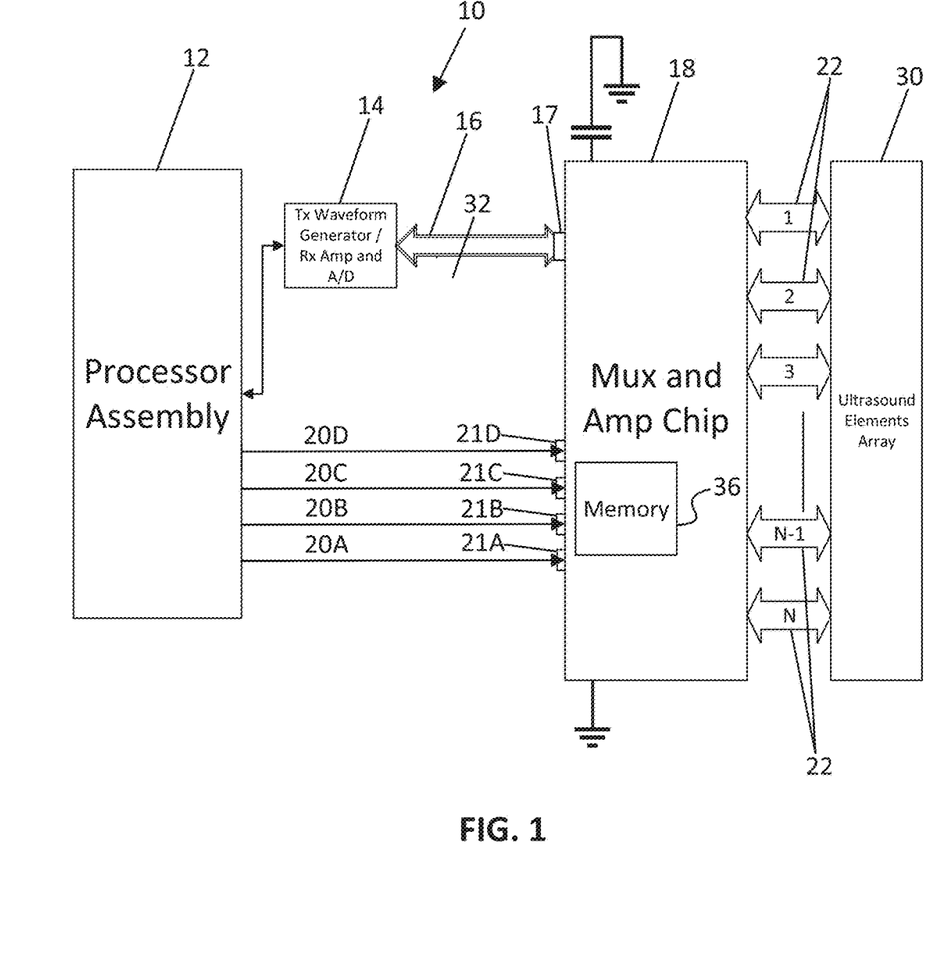
FIG. 1 is a block diagram of the ultrasound system of a medical device, according to the present invention.
Figure 2:
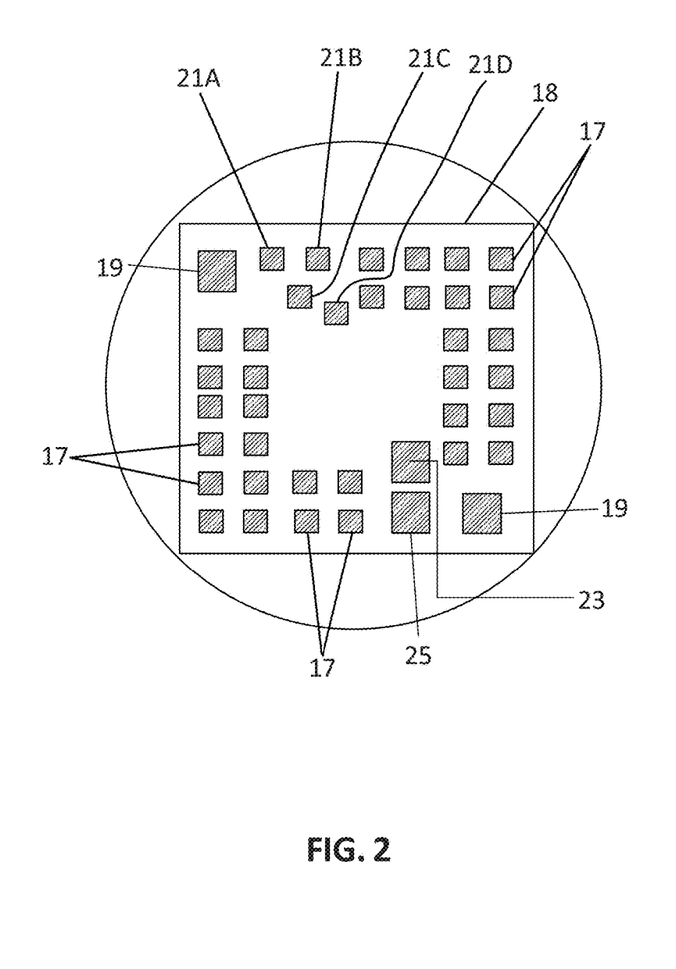
FIG. 2 is a physical representation of the proximal side of the mux and amp chip shown in block form in FIG. 1.
Figure 3:
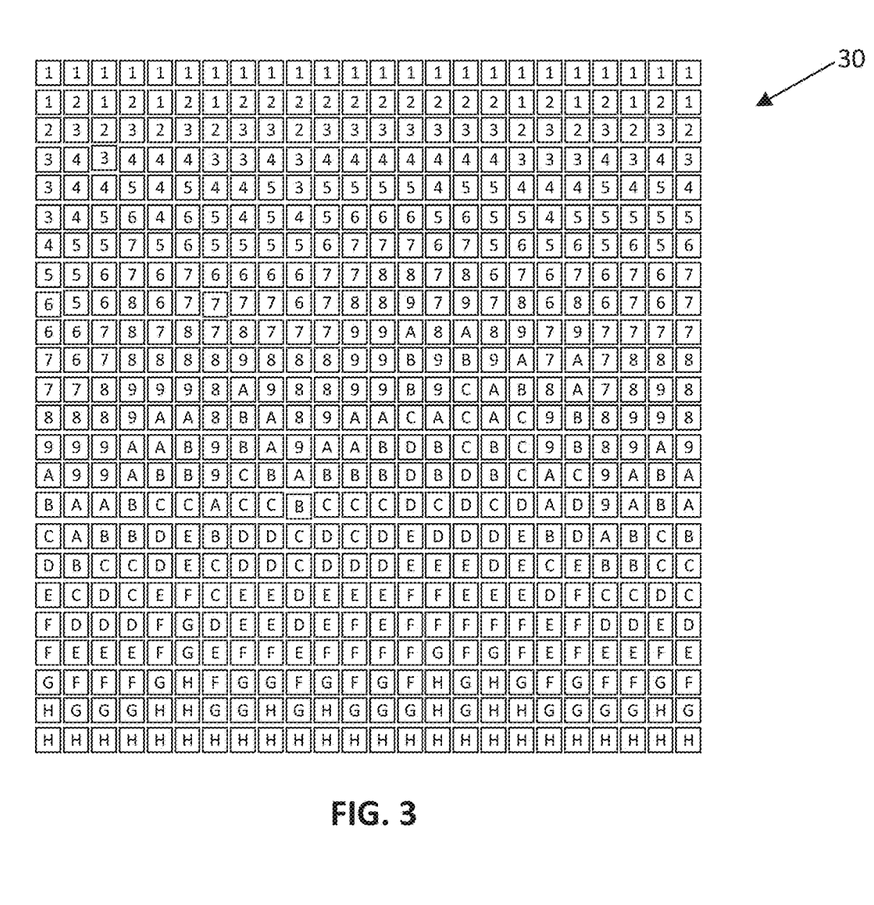
FIG. 3 is a proximal side view of the elements of the ultrasound array, shown in block form in FIG. 1, showing one allocation of ultrasound elements into eighteen blocks 1 through H.
Figure 4:
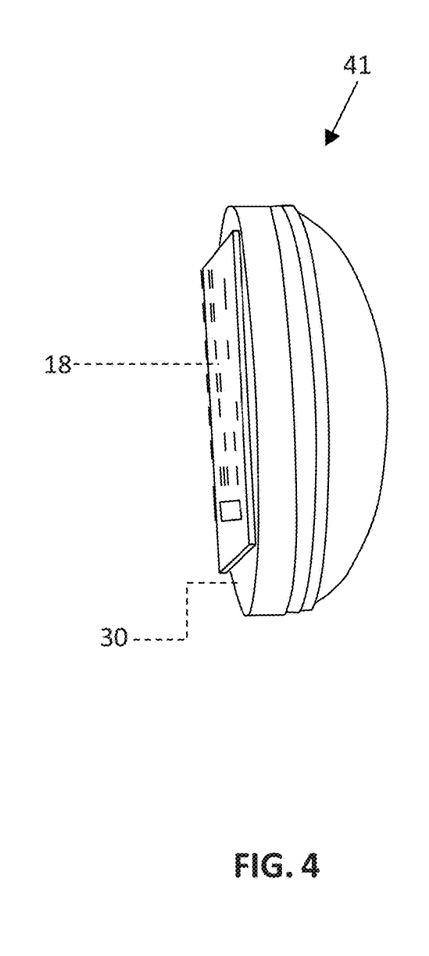
FIG. 4 is a side rear isometric view of the imaging head of the system of FIG. 1.
Figure 5:
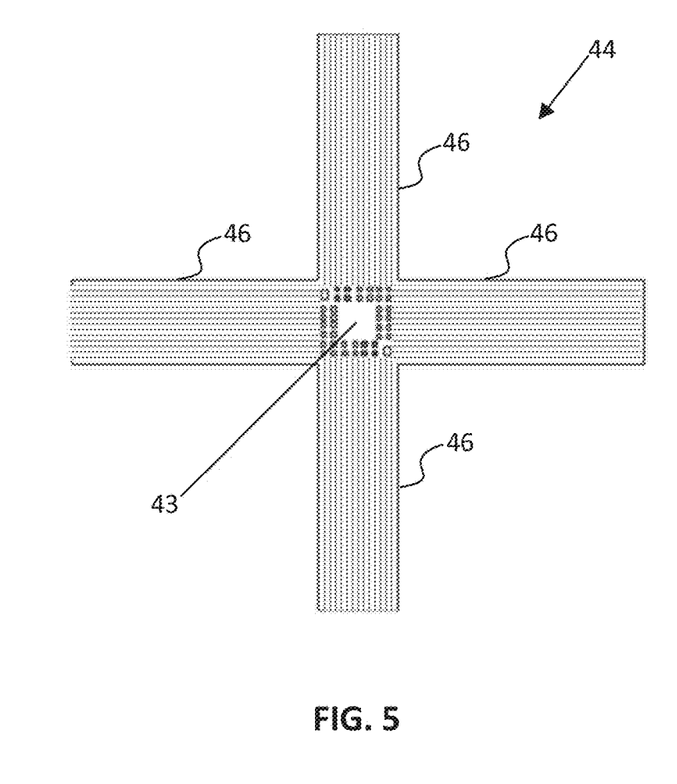
FIG. 5 is a view of an article of flex circuit used in the system of FIG. 1.

Referring to FIGS. 1 and 2, in a first preferred embodiment of an ultrasound imaging system 10, having a distal portion housed in a catheter sized to enter cardiac arteries, a processor assembly 12 commands a waveform signal generating network 14, which generates 35 MHz waveforms for 32 coax signal lines 16, which drive and receive from a set of 32 input/output contacts 17, on an integrated circuit die (henceforth "multiplexor chip" or "chip") 18. In one preferred embodiment, multiplexor chip 18 is less than 12 µm in thickness. In alternative embodiments, chip 18 is less than 20, 40, 60 and 80 µm. Control lines 20A-20D extend from processor 12 to multiplexor 18, attaching to contact pads 21A-21D, respectively, and must command multiplexor 18, for each phase to switch the 32 signal lines 16 to a one out of a set of 18 designated blocks 22 of drive/sense contacts, to drive one out of 18 blocks of thirty-two ultrasound elements in a 24×24 (576) ultrasound element array 30. In a preferred embodiment array 30 is made of a piezoelectric material, such as a piezoelectric ceramic. It is possible that at some point another technology, such as capacitive micromachined ultrasound transducers (CMUT)

may be usable in this application. Thirty-two micro-coax lines are required for the input/output contacts 17 with the grounds tied together and then eventually to a common ground (analog ground 19) on the chip. Plus, four more micro-coax are required for MUX control and power.

The basic function of the chip 18 is to allow 32 micro-coax acoustic channels to selectively connect to any thirty-two ultrasound array elements and to amplify the return signals from the ultrasound elements, as they are transmitted to the coax signal lines 16. On power-up the ultrasound system resets the chip 18 and asserts the Tx/Rx line placing the MUX in transmit mode for elements 1-32. The ultrasound system then transmits an electrical analog pulse through each of the micro-coax cables to contacts 17. The electrical pulses are then transferred to elements 1-32 of the piezoelectric array. After the ultrasonic pulses have left elements 1-32, the Tx/Rx line is de-asserted placing the MUX in receive mode. Mechanical energy reflected from the tissue or blood are converted to electrical energy by the piezoelectric elements 1-32 and the power transferred back through the chip 18 where the signal is amplified (using power received on contact pad 23), matched to the cable and sent back through each micro-coax to the ultrasound system for conversion to digital data at the front end of the imaging system. The Receive mode lasts for approximately 8 μS. Tx/Rx is then re-asserted and the cycle repeats for element 33-64 and so forth. A chip ground 25 is electrically connected to a further ground at the proximal end of a linear conductor.

In one scheme of driving the ultrasound element array 30, the following transmit receive sequence is performed, where $B_1$ is the first block of elements, $B_2$ is the second block of elements and so on until $B_{32}$ is the $32^{nd}$ block of elements and $TB_n$ indicates transmission through the nth block of elements, and $RB_n$ means receiving on the nth block of elements:

$TB_1$, $RB_1$, $TB_1$, $RB_2$, . . . , $TB_1$, $RB_n$, $TB_2$, $RB_1$, $TB_2$, $RB_2$, . . . $TB_2$, $RB_n$, . . . , $TB_nRB_1$, . . . $TB_nRB_n$ (S1)

In a catheter designed to be introduced into cardiac arteries, space is at a great premium, and any design aspects that reduce the number of lines that must extend through the catheter yield a great benefit. Although a traditional multi-plex device would permit any block 32 to be chosen at any time, this would require 5 control lines (yielding 32 combinations), not counting a transmit/receive choice line. Lowering the number of blocks to 16 would require blocks of 36—requiring four more coax signal lines 16, also difficult to fit into the catheter. To accommodate the above pattern of transmit and receive sequences, in one preferred embodiment control line 20b is a transmit line increment. In one preferred embodiment, chip 18 includes an incrementing register for transmit periods, incremented by a transmit increment line 20b and a separate incrementing register for receive periods, incremented by a receive increment line 20c. A transmit/receive selector line 20a thereby permits each to be incremented through its repeated cycles, as shown in sequence S1, listed above. In another embodiment, transmit/receive selector line 20a is used to increment the transmit and receive block registers, with for example, each rising edge counting as a transmit block increment and each falling edge counting as received block increments. A counter is placed in series with the transmit register so that only every 18th transition to transmit increments the transmit register and with every transition to receive incrementing the receive register, as indicated in sequence S1. This permits the transmit and receive increment lines to be eliminated. In yet another preferred embodiment, a single block increment line steps through the 18×18 (324) transmit/receive pairs sequence S1, which must be stored in a memory 36 of chip 18.

Figure 6:
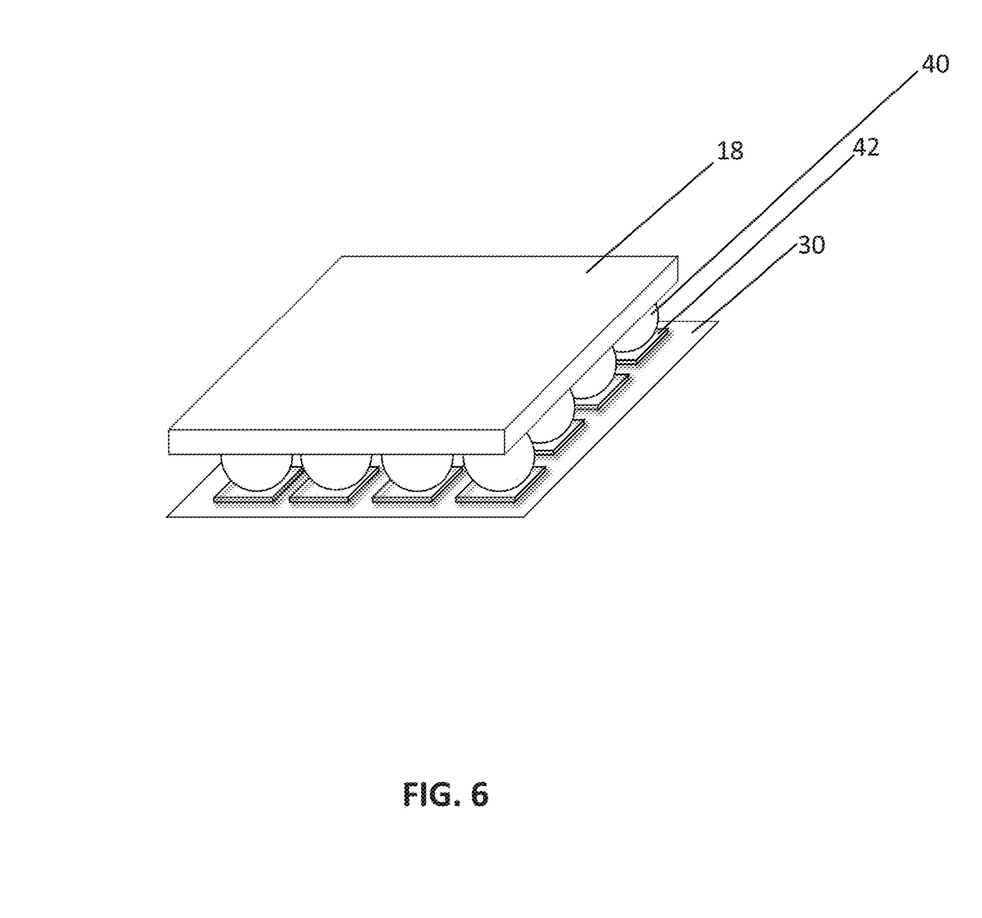
FIG. 6 is an illustration of the flip chip technique which may be used as a step in the production of the imaging head of FIG. 5.
Figure 7:
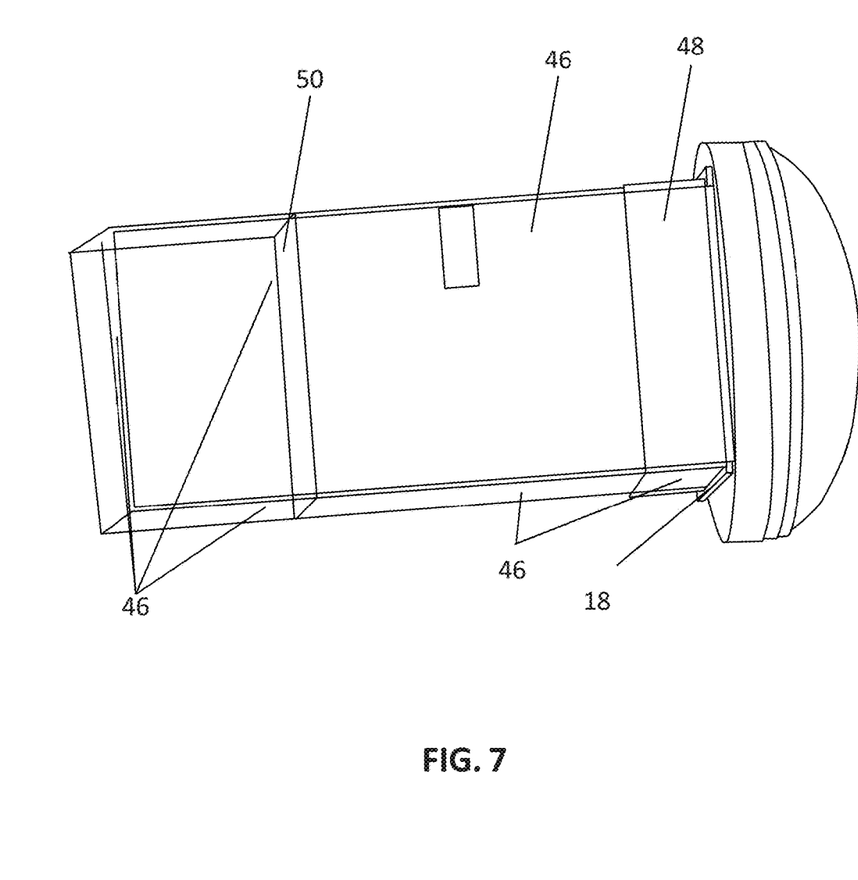
FIG. 7 is a side rear isometric view of the imaging head of FIG. 5, shown including further proximal elements.

Chip 18 is connected to array 30, by way of different techniques such as a flip chip bonding technique, pressure bonding through a thin layer of low viscosity adhesive (1-2 microns) or indium bonding. These are known techniques in the semiconductor/microchip industry. In the case of flip chip bonding, for example, a solder ball 40 (FIG. 6) is constructed on each chip contact 42, and then these solder balls 40 are pressed into array 30, slightly crushing solder balls 40, to form a good bond, and to create robust electrical connections between each chip contact 42, and each element of array 30. In this process, the thinness of chip 18 is a great advantage, because even though solder balls 40 have some thickness, the capability of chip 18 to bend slightly, due to its thinness, greatly facilitates the formation of a robust bond between solder balls 40 and each element of array 30. Adhesive filler is added among the thin solder balls 40 to increase strength as well as conduct acoustic energy into the dissipative backing. In the case of pressure bonding electrical conductivity is achieved through the surface roughness of the bonded substrates, the high points of which penetrate enough through the thin layer of adhesive to assure electrical connection. In the case of indium bonding conductive pads on both substrates (silicon chip and flex circuit) are metalized with a one to three thousand angstroms of indium which then flows through the application of heat at a low temperature (about 170 C). In addition, chip 18 is approximately 10 μm thick thus effectively becoming an "anti-matching" layer and an integral part of the acoustic architecture as opposed to a thicker chip. Computer simulations indicate that the thickness of the silicon chip can be further tweaked to achieve improved pulse properties.

The waveforms created by waveform generator 14 are typically two-cycle 35 MHz pulses, having pulse width of 5.7 nsec and pulse repetition frequency for 6 mm maximum penetration of 125 kHz or pulse repetition period of 8 usec. It should be noted that other frequencies in the range of 25 to 50 MHz may be utilized depending on resolution or penetration desired. In an embodiment, the IC die has a thickness of one-quarter of the waveform wavelength for said thin chip material.

Referring, now, to FIGS. 4, 5, 6 and 7, in one preferred embodiment, multiplex chip 18 forms a portion of an imaging and ablation head 41 as described in detail in U.S. Pat. No. 8,702,609. The proximal side of multiplex chip 18 is attached to a central portion 43 of a flex circuit 44, having four arms 46, that are bent proximally and that each include a number of the signal coax cables 16, and for which at least one includes one or more control lines, such as lines 20A-D. Ultrasound absorbent backing material 48 is proximal to central portion 42. This material is a polymer or polymer blend chosen for its ability to absorb high frequency ultrasound and in particular in the range of 20-50 MHz. The lossy backing material has the same acoustic impedance as the flex circuit material to avoid reflection at the interface between the two. Proximal to backing material 48 is a radiopaque marker 50. After extending proximally past marker 50, flex circuit arms 46 are connected to a group of coax cables and other conductors, for signals to travel to a base station (not shown).

Figure 8:
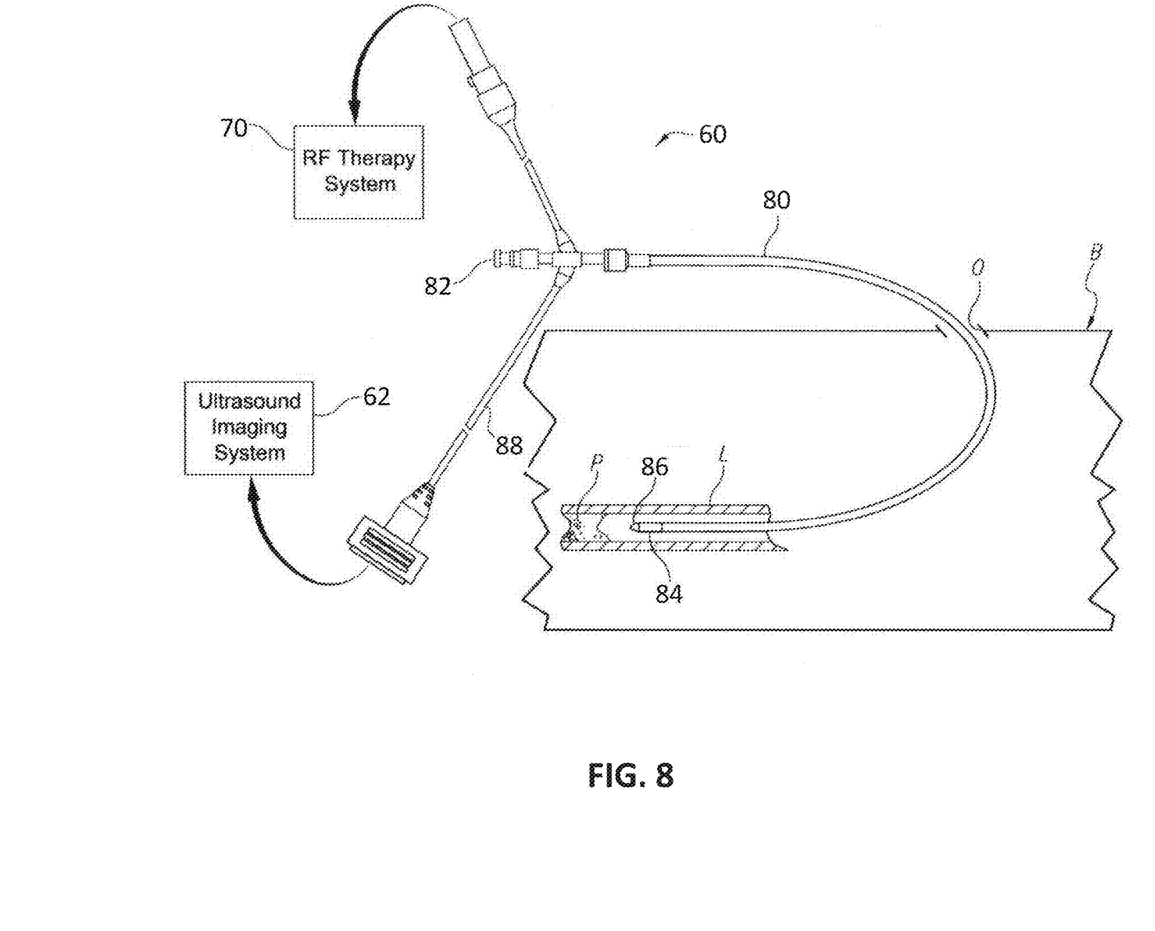
FIG. 8 is a diagram of a catheter configured for placement through an opening and into the body of a human patient or subject.

Referring to FIG. 8, in a preferred embodiment, ultrasound system 10 is physically implemented in a vascular imaging and plaque ablation catheter system 60. System 60 is arranged to provide images internal to body B for medical diagnosis and/or medical treatment. System 60 includes a control station comprising an ultrasound imaging system 62, of which processor assembly 12 and waveform generator and receive amplifier 14 form a portion, and an RF therapy system 70, each of which are operatively coupled to catheter 80, as well as appropriate operator input devices (e.g. keyboard and mouse or other pointing device of a standard variety) and operator display device (e.g. CRT, LCD, plasma screen, or OLED monitor).

Catheter 80 is configured for placement through opening O and into body B of a human patient or subject, as schematically represented in FIG. 8. Catheter 80 is preferably configured for insertion into a blood vessel or similar lumen L of the patient by any conventional vascular insertion technique. Catheter 80 includes a guide wire lumen that extends from a proximal port 82 through the distal tip 84 of the catheter 80, which is used to insert catheter 80 over a pre-inserted guidewire (not shown) via a conventional over the wire insertion technique. The guidewire exit port may be spaced proximally from the distal tip, accordingly to known design. Catheter 80 may be configured with a shortened guidewire lumen so as to employ a monorail type insertion technique, or catheter 80 may be configured without any guidewire lumen and instead configured for insertion through the lumen of a pre-inserted guide catheter.

The mux and amp chip 18 and ultrasound elements array 30 are located in distal end 84, whereas a set of RF ablation electrodes (not shown) form distal tip 86, which is designed to ablate arterial plaque P. Mini coax cables 16 extend through a side cable 88 and then through a lumen in catheter 80, together with control signal wires 20A-20D (which in one embodiment extend through the flexible exterior wall of catheter 80). Skilled persons will readily recognize that this entails the transmission of ultrasound signals from array 30 through the ablation electrodes.

While a number of exemplary aspects and embodiments have been discussed above, those possessed of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

The invention claimed is:

1. An intravenous ultrasound catheter having a distal tip and comprising:
   (a) a forward-facing array of ultrasound elements near to said distal tip of said device;
   (b) an integrated circuit (IC) die, abutting and proximal to said ultrasound elements, having a thickness of less than 80 μm, and having:
      (i) a first face, facing said forward-facing array, and having an array of ultrasound element driving and receiving contacts, in mating arrangement to said array of ultrasound elements, so that said array of ultrasound element driving and receiving contacts collectively physically abut and electrically connect to each of said ultrasound elements;
      (ii) a second face, opposed to said first face, and having a set of input-output signal contacts, said set being fewer in number than said array of ultrasound element driving and receiving contacts and being collectively switchable into contact with any one of a set of predefined blocks of said ultrasound element driving and receiving contacts, said second face also having a set of control contacts, wherein inputs received by said control contacts positively collectively command some aspect of operation of said IC die; and
      (iii) wherein said ultrasound element driving and receiving contacts can send and receive signals from a first one of said blocks of said driving and receiving contacts and can then be switched to send and receive signals from a second one of said blocks of said driving and receiving contacts, different from said first one of said blocks;
   (c) a flex circuit assembly, proximal to said integrated circuit and including coax cables and a contact portion, having a set of contact pads abutting and electrically connecting said input-output signal contacts of said IC die, to said coax cables;
   (d) backing material, abutting and directly proximal to said contact portion, thereby forming an interface and wherein said backing material and said contact portion material have equal acoustic impedance, thereby preventing reflection at said interface; and
   (e) a tubular flexible protective covering, covering said array of ultrasound elements, said integrated circuit die, said flex circuit assembly and said backing material.

2. The intravenous ultrasound catheter of claim 1, sized to fit into coronary arteries.

3. The intravenous ultrasound catheter of claim 1, also including a distal tip having RF ablation electrodes.

4. The intravenous ultrasound catheter of claim 1, wherein said flex circuit assembly splits apart into separate arms of flex circuit that extend proximally, beyond the extent of said backing material from said contact portion, each arm including some of said coax cables.

5. The intravenous ultrasound catheter of claim 1, wherein said integrated circuit die has a thickness of less than 20 μm.

6. The intravenous ultrasound catheter of claim 1, wherein one or more of said control contacts are multiplex control contacts and wherein signals received over said multiplex control contacts specifically command which block, chosen from said group of predefined blocks of ultrasound elements, will have receive signals sent to said input/output contacts.

7. The intravenous ultrasound catheter of claim 6, wherein signals received over said multiplex control contacts command said IC die to progress through a prespecified sequence of predefined blocks of driving and receiving contacts, receiving input, sequentially, from said blocks of driving and receiving contacts.

8. The intravenous ultrasound catheter of claim 1, wherein said IC die includes computer readable nontransitive memory having at least two predefined time patterns of driving and receiving from said predefined blocks of ultrasound array driving and receiving contacts, and wherein signals received over said set of control contacts command which pattern out of said at least two predefined patterns is to be currently used.

9. The intravenous ultrasound catheter of claim 1, wherein said IC die includes an amplifier for each one of said driving and receiving electrical contacts, adapted to amplify received ultrasound signals.

10. The intravenous ultrasound catheter of claim 1, wherein said flex circuit assembly has an input/output line for each input/output contact.

11. The intravenous ultrasound catheter of claim 10, wherein said flex circuit contact portion further includes contact pads for said control contacts of said IC die and also includes arms having said coax cable extending therein and serving as signal lines for carrying signals from and to said IC die.

12. The intravenous ultrasound catheter of claim 1, wherein said ultrasound array includes more than 256 elements and has dimensions of less than 2 mm by 2 mm.

13. The intravenous ultrasound catheter of claim 1, further including a set of ablation electrodes, positioned forward of said array of ultrasound elements so that said ultrasound elements transmit and receive through said set of ablation electrodes.

14. The intravenous ultrasound catheter of claim 1, wherein said array of ultrasound element driving and receiving contacts is flip chip bonded to said array of ultrasound elements.

15. The intravenous ultrasound catheter of claim 1, further including a coax cable for each input/output contact.

16. The intravenous ultrasound catheter of claim 1, further including a waveform generator, generating a waveform having a frequency of between 20 MHz and 40 MHz, and wherein said IC die has a thickness of one-quarter of the waveform wavelength for said IC die material.

17. The intravenous ultrasound catheter of claim 1, further including RF ablation electrodes positioned distal to said ultrasound elements.

18. The intravenous ultrasound catheter of claim 1, wherein said IC die has a thickness of less than 12 μm.

* * * * *